United States Patent [19]

Shibayama et al.

[11] Patent Number: 5,478,823

[45] Date of Patent: Dec. 26, 1995

[54] COMPOSITION FOR SUPPRESSING INFILTRATION OF EOSINOPHILS

[75] Inventors: Katsuhiro Shibayama; Naoki Hirayama; Tetsuya Katou; Shu Matsumoto, all of Kamakura, Japan

[73] Assignee: Toray Industries, Inc., Tokyo, Japan

[21] Appl. No.: 244,891

[22] PCT Filed: Oct. 18, 1993

§ 371 Date: PCT/JP93/01492

§ 371 Date: Aug. 22, 1994

§ 102(e) Date: Aug. 22, 1994

[87] PCT Pub. No.: WO94/08581

PCT Pub. Date: Apr. 28, 1994

[30] Foreign Application Priority Data

Oct. 20, 1992 [JP] Japan .................................. 4-281653

[51] Int. Cl.[6] .................... A61K 31/55; A61K 31/495; A61K 31/50; A61K 31/445; A61K 31/41

[52] U.S. Cl. .................... 514/214; 514/220; 514/250; 514/253; 514/322; 514/383

[58] Field of Search .................... 514/214, 220, 514/250, 253, 322, 383

[56] References Cited

FOREIGN PATENT DOCUMENTS 536419 4/1992 European Pat. Off. .
49-4478 1/1974 Japan .

OTHER PUBLICATIONS

Drug Des Deliv., vol. 5, No. 1, 1989, H. O. Heuer, "Hetrazepinoic antagonists of platelet activating factor," pp. 31–47.

*Primary Examiner*—Kimberly Jordan

*Attorney, Agent, or Firm*—Birch, Stewart, Kolasch & Birch

[57] ABSTRACT

An agent for suppressing infiltration of eosinophils comprising as an effective ingredient a tricyclic triazolo derivative, which strongly suppresses infiltration of eosinophils into inflammatory regions, of the formula (I):

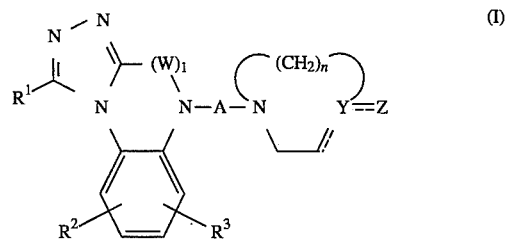

wherein $R^1$ represents hydrogen, lower alkyl, $C_3$–$C_5$ cycloalkyl or substituted or non-substituted aryl; $R^2$ and $R^3$ independently represent hydrogen, lower alkyl, lower alkoxy or halogen; W represents C=O or $CR^4R^5$ wherein $R^4$ and $R^5$ independently represent hydrogen or lower alkyl; A represents $C_1$–$C_5$ straight or branched saturated or unsaturated alkylene with the proviso that it may contain one or more hetero atoms; l represents 0 to 2, n represents 1 to 3, — represents single bond or double bond; Y represents N or C; Z represents $C(B)Ar^1Ar^2$ wherein B represents hydrogen, hydroxy or methoxy, $Ar^1$ and $Ar^2$ independently represent hydrogen or substituted or non-substituted aryl, $CAr^1Ar^2$ wherein $Ar^1$ and $Ar^2$ represent the same meanings as mentioned above, O—$CHAr^1Ar^2$ wherein $Ar^1$ and $Ar^2$ represent the same meanings as mentioned above or a condensed aromatic ring or a pharmaceutically acceptable salt thereof.

8 Claims, No Drawings

COMPOSITION FOR SUPPRESSING INFILTRATION OF EOSINOPHILS

This application is a 371 of PCT/JP93/01492, filed Oct. 18, 1993.

BACKGROUND OF THE INVENTION

1. Field of the Invention

The present invention relates to a composition for suppressing infiltration of eosinophils comprising as an effective ingredient a tricyclic triazolo derivative, which strongly suppresses infiltration of eosinophils into inflammatory regions.

2. Description of the Related Art

Recently, it was found that eosinophils play an important role in passing allergic diseases such as bronchial asthma into a chronic state. For example, in bronchoalveolar lavage fluid (BALF) obtained several hours after an asthma attach caused by having a patient inhale an antigen, an increase in the number of eosinophils is observed. It is suggested that eosinophils play an important role in damaging tissues due to the presence of histotoxic proteins such as major basic protein (MBP) and eosinophil cationic protein (ECP) in granules [SAISHIN IGAKU, Vol. 45, No. 3, SAISHIN IGAKUSHA]. Therefore, it is expected that a compound which suppresses infiltration of eosinophils has therapeutic effect against allergic diseases, such as bronchial asthma.

A novel and useful eosinophil infiltration suppressor is expected to have therapeutic effect against allergic diseases such as bronchial asthma, and is demanded.

SUMMARY OF THE INVENTION

An object of the present invention is to provide an eosinophil infiltration suppressor which is also useful as an anti-inflammatory agent or anti-allergic agent.

That is, the present invention provides a composition for suppressing infiltration of eosinophils comprising as an effective ingredient a tricyclic triazolo derivative of the formula (I):

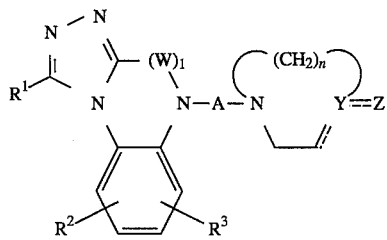

wherein $R^1$ represents hydrogen, lower alkyl, $C_3-C_5$ cycloalkyl or substituted or non-substituted aryl; $R^2$ and $R^3$ independently represent hydrogen, lower alkyl, lower alkoxy or halogen; W represents C=O or $CR^4R^5$ (wherein $R^4$ and $R^5$ independently represent hydrogen or lower alkyl); A represents $C_1-C_5$ straight or branched saturated or unsaturated alkylene (with the proviso that it may contain one or more hetero atoms); l represents 0 to 2, n represents 1 to 3, — represents single bond or double bond; Y represents N or C; Z represents $C(B)Ar^1Ar^2$ (wherein B represents hydrogen, hydroxy or methoxy, $Ar^1$ and $Ar^2$ independently represent hydrogen or substituted or non-substituted aryl), $CAr^1Ar^2$ (wherein $Ar^1$ and $Ar^2$ represent the same meanings as mentioned above), $O—CHAr^1Ar^2$ (wherein $Ar^1$ and $Ar^2$ represent the same meanings as mentioned above) or a condensed aromatic ring or a pharmaceutically acceptable salt thereof.

As is apparent from the examples described below, the agent for suppressing infiltration of eosinophils according to the present invention exhibits strong eosinophil infiltration-suppressing activity. Therefore, by using the agent for suppressing infiltration of eosinophils according to the present invention, prevention and therapy of the diseases in which eosinophils participate (such as asthma, inverminations, tumors, eosinophilic leukemia, eosinophila syndrome, eosinophilic pneumonia, and eosinophilic gastroenteritis) can be attained.

DETAILED DESCRIPTION OF THE INVENTION

As mentioned above, the composition for suppressing infiltration of eosinophils according to the present invention comprises as an effective ingredient the tricyclic triazolo derivative represented by the above-described formula (I) or a pharmaceutically acceptable salt thereof.

In the definitions of the symbols in the above-described formula (I), halogen means fluorine, chlorine, bromine and iodine. The alkyl moiety in lower alkyl and lower alkoxy means $C_1-C_6$ straight or branched alkyl such as methyl, ethyl, n-propyl, isopropyl, n-butyl, isobutyl, t-butyl and n-pentyl. Among these, methyl and ethyl are preferred. In the definition of "A", $C_1-C_5$ straight or branched saturated or unsaturated alkylene means methylene, ethylene, propylene and the following structures:

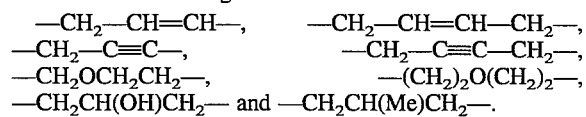

The aryl represented by $Ar^1$ or $Ar^2$ in the definition of Z and the aryl in the definition of $R^1$ represent $C_6-C_{10}$ aryl such as phenyl and naphthyl, and includes aromatic heterocyclic groups such as 2-pyridyl, 3-pyridyl, 2-pyrimidyl, 2-thienyl and 2-furyl. In the above-mentioned definitions, substituent group means the same or different 1–3 substituent groups on the aromatic ring, selected from the group consisting of $C_1-C_6$ alkyl, $C_1-C_6$ alkoxy, halogen, $C_1-C_6$ haloalkyl, $C_1-C_6$ alkylamino and nitro. Thus, substituted aryl means 4-chlorophenyl, 4-bromophenyl, 4-fluorophenyl, 4-methylphenyl, 4-methoxyphenyl, 4-trifluoromethylphenyl, 5-methyl-2-thienyl, 2,3-dichlorophenyl, 3,4,5-trimethoxyphenyl and the like. Condensed aromatic ring means naphthalene, quinoline, benzimidazole, benzofuran, benzothiophene, benzisoxazole, benzthiazole, imidazopyridine and the like. Preferred are those selected from the following groups:

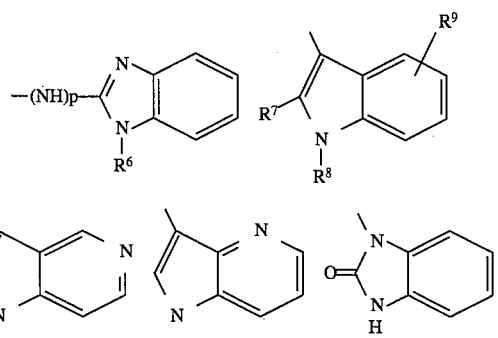

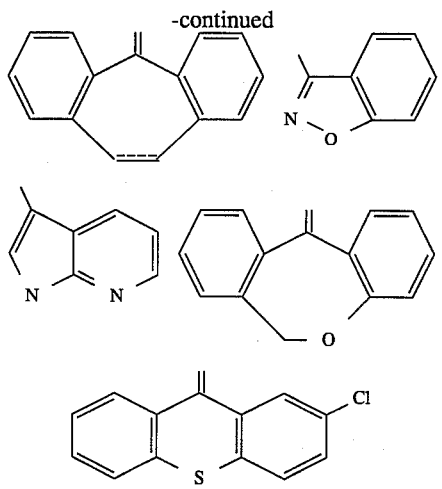

wherein R⁶ represents substituted or non-substituted aralkyl or alkoxyalkyl; p represents 0 or 1; R⁷ and R⁸ independently represent hydrogen or lower alkyl; R⁹ represents hydrogen, lower alkyl, lower alkoxy or halogen; and — represents single bond or double bond. In the above-described definition, substituted or non-substituted aralkyl means benzyl, 4-fluorobenzyl, 4-chlorobenzyl, 2-thienylmethyl, 2-furylmethyl and the like, and 4-fluorobenzyl is preferred. Alkoxyalkyl means ethoxyethyl, methoxyethyl, methoxypropyl and the like, and ethoxyethyl is preferred. Lower alkyl and halogen have the same meanings as described above.

The pharmaceutically acceptable salts of the compound of the formula (I) include inorganic acid salts such as hydrochloric acid salt, hydrobromic acid salt, sulfuric acid salt, boric acid salt and phosphoric acid salt; organic acid salts such as acetic acid salt, maleic acid salt, fumaric acid salt, tartaric acid salt, succinic acid salt, malic acid salt and p-toluenesulfonic acid salt; and amino acid addition salts including lysine, glycine, phenylalanine and the like.

In cases where the tricyclic triazolo derivative employed in the present invention has one or more asymmetric carbon atoms, racemates, diastereomers and optical isomers may exist. In the present invention, any of these can be employed.

The tricyclic triazolo derivatives represented by the formula (I) can be prepared by the method described in WO 92/18505 or EP 0 536 419 A1.

By using the tricyclic triazolo derivative or a pharmaceutically acceptable salt thereof according to the present invention, it is expected that prevention and therapy of allergies and inflammation, as well as other various diseases in which eosinophils are thought to participate, may be attained. More particularly, they can also be used as therapeutic agents for treating asthma, inverminations, tumors, eosinophilic leukemia, eosinophila syndrome, eosinophilic pneumonia, and eosinophilic gastroenteritis.

The compounds represented by the formula (I) and acid addition salts thereof may be administered orally or parenterally to mammals in the form of formulations appropriate as pharmaceutical compositions.

Examples of the formulations for oral administration include tablets, pills, powders, capsules, granules, medicated syrups, emulsions and suspensions. These formulations may be prepared by the known methods and contain carriers or vehicles usually used in the formulations. For example, as the carrier or vehicle of tablets, lactose, starch, sucrose, magnesium stearate and the like may be employed.

Examples of the formulations for parenteral administration include ointments, injection solutions, fomentations, liniments, inhalants, suppositories, formulations for percutaneous absorption and the like. The injection solution may be formulated according to known methods. For example, the injection solution may be formulated by dissolving, suspending or emulsifying the compound of the formula (I) or a salt thereof in aseptic aqueous or oily solution usually used in injection solutions. Examples of the aqueous solution for injection include physiological saline and glucose solution, and examples of the oily solution include sesame oil and soybean oil. Solubilizers may be added to the injection solutions. The suppositories used for rectal administration may be formulated by, for example, mixing the compound of the formula (I) or a salt thereof with a usual base for suppositories and molding the mixture.

Although the effective dose and the number of administration of the compound of the formula (I) and the pharmaceutically acceptable salts thereof vary depending on the administration route, age and body weight of the patient and on the property and the degree of the disease to be treated, usually, 0.1–1000 mg, preferably 1–200 mg of the compound may be administered per day per an adult in one time or in several times.

The above-described formulations may contain other effective ingredients for the treatment of other diseases as long as undesired interactions are not brought about by the combination of the compound of the formula (I) or the pharmaceutically acceptable salts thereof and the other effective ingredients. Examples of such effective ingredient include steroid agents, non-steroid anti-inflammatories, lipoxygenase inhibitors, leucotriene antagonists, bronchodilators, thromboxane synthesis inhibitors, histamine release inhibitors, serotonin antagonists, adenosine receptor antagonists, adrenergic β-receptor antagonists, immunosuppressive agents, immunomodulators and the like.

An example of the composition of a tablet containing the compound of the present invention is described below.
Formulation Example Tablet A tablet having the following composition is formulated according to a conventional method.

| | |
|---|---|
| Compound of Example 1 | 20 mg |
| Lactose | 80 mg |
| Corn Starch | 30 mg |
| Polyvinyl Alcohol | 2 mg |
| Magnesium Stearate | 1 mg |
| Tar Pigment | Trace Amount |

The effect of the present invention will now be described by way of examples below. It should be noted, however, the present invention is not limited by the examples.

REFERENCE EXAMPLE 1

1,2-dihydroquinoxaline-3(4H)-thione

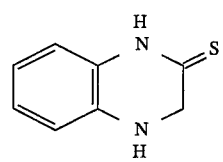

To 52 g of 1,2-dihydro-3-hydroxyquinoxaline, 47 g phosphorus pentasulfide and 59 g of sodium hydrogen carbonate, 280 ml of Diglyme was added and the mixture was stirred at 60° C. for 1 hour. The solvent was evaporated under reduced pressure and 500 ml of water was added to the residue. Crystals were collected by filtration and washed to obtain 47 g of the captioned compound as yellow green crystals. The crystals were recrystallized from benzene to obtain the captioned compound.

mp: 120°–123° C. IR (KBr) cm$^{-1}$: 3250, 3180, 3100, 2970, 1562, 1510, 1307 $^1$HNMR (CDCl3) δ: 9.75(1H,br s), 7.12–6.64(4H,m), 4.33(2H,s)

REFERENCE EXAMPLE 2

4,5-dihydro-1-methyl[1,2,4]triazolo[4,3-a]quinoxaline

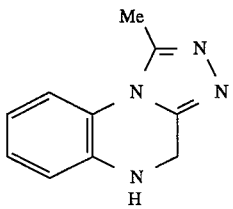

To 62 g of the compound obtained in Reference Example 1 and 56 g of acetohydrazide, 750 ml of n-butanol was added and the mixture was heated to reflux for 4 hours. The solvent was evaporated under reduced pressure and water was added to the residue, followed by extraction of the resulting mixture with dichloromethane. The organic layer was washed with water and dried. The solvent was evaporated under reduced pressure and the product was recrystallized from isopropanol to obtain 49 g of the captioned compound as pale brown needle-shaped crystals.

mp: 173°–174° C. IR (KBr) cm$^{-1}$: 3230, 1562, 1510, 1499, 1431 $^1$HNMR (CDCl3) δ: 7.50–6.82(4H,m), 4.58(2H, d,J=1.8), 4.18(1H,br s), 2.78(3H,s) MS:186 (M+)

REFERENCE EXAMPLE 3

1-(3-chloropropyl)-4-(diphenylmethylene)piperidine

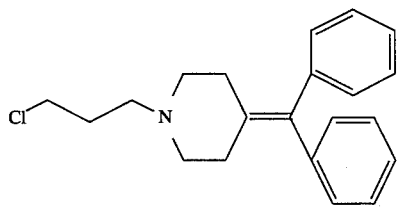

To 4.03 g of 4-(diphenylmethylene)piperidine and 6.37 g of 1-bromo-3-chloropropane, 20 ml of toluene, 10 ml of 25% sodium hydroxide solution and 0.27 g of tetrabutylammonium hydrogensulfate were added and the mixture was stirred at room temperature for 10 hours. The resultant was extracted with ethyl acetate and the organic layer was washed with water and dried. After evaporating the solvent under reduced pressure, the product was recrystallized from cyclohexane to obtain 3.67 g of the captioned compound as colorless crystals.

mp: 73°–73.5° C. IR (KBr) cm$^{-1}$: 2922, 2772, 1491, 1441, 1377, 1296, 1122, 996, 760, 702 $^1$HNMR (CDCl3) δ: 7.3–7.0(10H,m), 3.60(2H,t,J=7), 2.6–2.4(6H,m), 2.4–2.3(4H,m), 1.96(2H,quint,J=7)

EXAMPLE 1

4,5-dihydro-1-methyl-5-[3-[4-(diphenylmethylene)-piperidine-1-yl]propyl][1,2,4]triazolo[4,3-a]quinoxaline

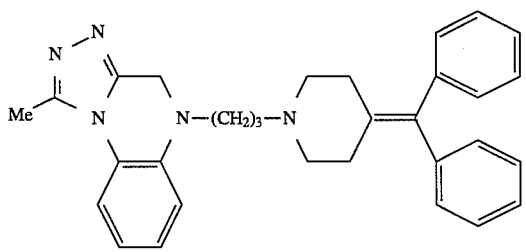

In 50 ml of dimethylformamide, 3.53 g of the compound obtained in Reference Example 2 and 6.18 g of the compound obtained in Reference Example 3 were dissolved and the resulting mixture was cooled to −20° C. To the resultant, 20 ml of t-BuOK solution (1M) in dimethylformamide was added and the resulting mixture was stirred at room temperature for 3 hours. Saturated aqueous ammonium chloride solution was added and the obtained precipitates were separated by filtration and recrystallized from n-butanol to obtain 6.32 g of the captioned compound as colorless crystals.

mp: 204°–205° C. Elementary Analysis: C31H33N5 Calcd.: C,78.28; H,6.99; N,14.73 Found: C,78.14; H,7.10; N,14.65 IR (KBr) cm$^{-1}$: 2892, 1508, 1429, 1348, 745, 704 $^1$HNMR (CDCl3) δ: 7.45(1H,dd,J=8.1,1.1), 7.28(4H,t,J= 7.0), 7.21(3H,q,J=7.3), 7.12(4H,d,J=7.0), 6.98(1H,d,J=8.4), 6.90(1H,t,J=7.9), 4.44(2H,s), 3.41(2H,t,J=7.3), 2.77(3H,s), 2.53(4H,br s), 2.44(6H,m), 1.90(2H,quint,J=7.0) MS:475(M+)

EXAMPLE 2

4,5-dihydro-1-methyl-5-[3-[4-(diphenylmethylene)-piperidine-1-yl]propyl][1,2,4]triazolo[4,3-a]quinoxaline maleic acid salt

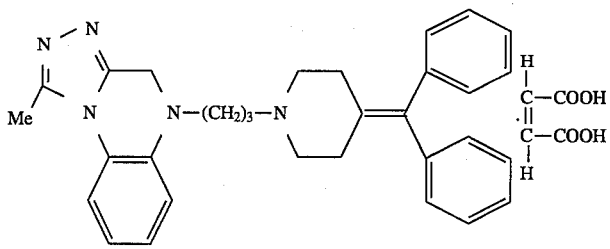

In 1.5 liters of ethanol, 20 g of the compound obtained in Example 1 and 4.88 g of maleic acid were dissolved under heat. After dissolving the compound, the resulting solution was allowed to cool to room temperature. After cooling the mixture, precipitated crystals were collected by filtration and dried to obtain 20.3 g of the captioned compound as white crystals.

mp: 193°–195° C. Elementary Analysis: C31H34N5.C4H4O4 Calcd.: C,78.28; H,6.99; N,14.72 Found: C,78.27; H,7.05; N,14.76 IR (KBr) cm$^{-1}$: 3650, 3041, 2995, 2604, 2450, 1702, 1578, 1473, 1350, 866, 756, 700 $^1$HNMR (CD3OD) δ: 7.65(1H,dd,J=7.8,1.0), 7.33–7.30(5H,m), 7.26–7.23(2H,m), 7.14–7.08(5H,m), 7.03(1H,t,J=7.3), 6.23(2H,s), 4.41(2H,s), 3.49(2H,t,J=6.8), 3.33–3.19(6H,m), 2.75(3H,s), 2.68–2.52(4H,m), 2.15(2H,m)

mp: 128°–136° C. Elementary Analysis: C31H34N5.1.5(C4H6O6).1.0H2O Calcd.: C,61.83; H,6.17; N,9.74 Found: C,61.92; H,6.20; N,9.69 IR (KBr) cm$^{-1}$: 3322, 1738, 1599, 1562, 1504, 1421, 1309, 1267, 760, 704 $^1$HNMR (CD3OD) δ: 7.65(1H,dd,J=7.8,1.0), 7.33–7.30(5H,m), 7.26–7.23(2H,m), 7.14–7.02(5H,m), 4.44(3H,s), 4.42(2H,s), 3.48(2H,t,J=6.7), 3.33–3.19(6H,m), 3.31(3H,s), 2.65–2.62(4H,m), 2.15(2H,m)

EXAMPLE 3

4,5-dihydro-1-methyl-5-[3-[4-(diphenylmethylene)-piperidine-1-yl]propyl][1,2,4]triazolo[4,3-a]quinoxaline (d)-tartaric acid.monohydrate

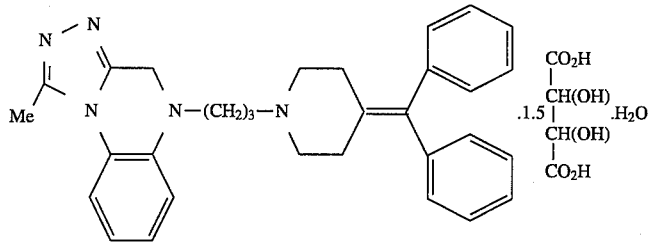

In the same manner as in Example 2, 4.78 g of the compound obtained in Example 1 and 2.26 g of (d)-tartaric acid were dissolved in ethanol solvent under heat to obtain 5.93 g of the captioned compound as white crystals.

EXAMPLE 4

4,5-dihydro-1-methyl-5-[3-[4-(diphenylmethylene)-piperidine-1-yl]propyl][1,2,4]triazolo[4,3-a]quinoxaline (1)-malic acid salt hemihydrate

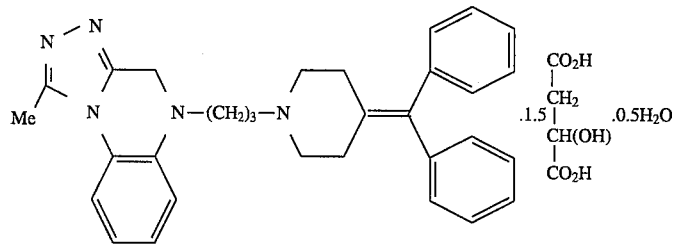

In the same manner as in Example 2, 4.45 g of the compound obtained in Example 1 and 2.26 g of (1)-malic acid were dissolved in n-butanol solvent under heat to obtain 1.58 g of the captioned compound as white crystals.

mp: 128°–135° C. Elementary Analysis: C31H34N5.1.5(C4H6O5).0.5H2O Calcd.: C,64.80; H,6.32; N,10.21 Found: C,64.57; H,6.44; N,10.35 IR (KBr) cm$^{-1}$: 3420, 1719, 1562, 1504, 1433, 1284, 1114, 752, 706 $^1$HNMR (CD3OD) δ: 7.65(1H,dd,J=6.7,1.2), 7.33–7.30(5H, m), 7.26–7.23(2H,m), 7.14–7.01(5H,m), 4.43(2H,s), 3.48(2H,t,J=7.2), 3.33–3.19(5H,m), 2.76(3H,s), 2.65(3H,t,J=6.1), 2.18(2H,m)

EXAMPLE 5

4,5-dihydro-1-methyl-5-[3-[4-(diphenylmethylene)-piperidine-1-yl]propyl][1,2,4]triazolo[4,3-a]quinoxaline fumaric acid salt

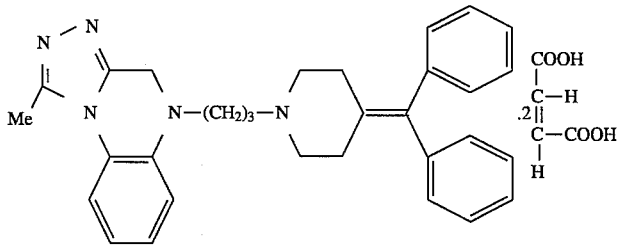

In the same manner as in Example 2, 0.50 g of the compound obtained in Example 1 and 0.35 g of fumaric acid were dissolved in ethanol solvent under heat to obtain 0.41 g of the captioned compound as white crystals.

Elementary Analysis: C31H34N5.2(C4H4O4) Calcd.: C,66.16; H,5.84; N,9.89 Found: C,66.11; H,5.86; N,9.82 IR (KBr) cm$^{-1}$: 3641, 3022, 1731, 1574, 1350, 821, 740, 705 $^1$HNMR (CD3OD) δ: 7.67(1H,dd,J=7.8,1.0), 7.34–7.30(5H, m), 7.26–7.23(2H,m), 7.15–7.09(5H,m), 7.04(1H,t,J=7.6), 6.71(4H,s), 4.42(2H,s), 3.49(2H,t,J=6.8), 3.31–3.17(6H,m), 2.76(3H,s), 2.62(4H,t,J=6.0), 2.15(2H,m)

EXAMPLE 6

4,5-dihydro-1-methyl-5-[3-[4-(diphenylmethylene)-piperidine-1-yl]propyl][1,2,4]triazolo[4,3-a]quinoxaline phosphoric acid salt

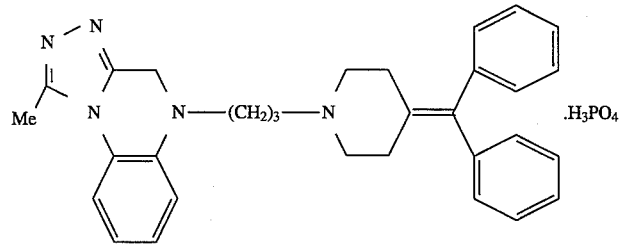

In the same manner as in Example 2, 0.45 g of the compound obtained in Example 1 and 0.41 g of phosphoric acid were dissolved in ethanol solvent under heat to obtain 0.41 g of the captioned compound as white crystals.

mp: 133°–137° C. Elementary Analysis: C31H34N5.H3PO4 Calcd.: C,64.91; H,6.32; N,12.21; P,5.40 Found: C,62.63; H,6.80; N,11.78; P,5.09 IR (KBr) cm$^{-1}$: 3633, 3051, 2821, 1731, 1522, 1322, 821, 741, 701 $^1$HNMR (CD3OD) δ: 7.65(1H,dd,J=7.9,1.2), 7.34–7.30(5H, m), 7.25–7.22(2H,m), 7.14–7.11(5H,m), 7.03(1H,t,J=1.2), 4.43(2H,s), 3.48(2H,t,J=6.8), 3.41–3.22(6H,m), 2.76(3H,s), 2.66(4H,t,J=6.1), 2.17(2H,m)

EXAMPLE 7

Eosinophil Infiltration-Suppressing Activity

Hartley male guinea pigs of 4 weeks old were purchased from NIPPON SLC. After one week's acclimatization, sensitization was started. That is, 100 mg/kg of cyclophosphamide was intraperitoneally administered to each guinea pig. Twenty four hours after the administration, 1 ml of alum suspension containing 10 μg of ovalbumin (OVA) and 5×10$^9$ cells of inactivated *Bordetella pertussis* was intraperitoneally administered. A second sensitization was performed in the same manner 2 weeks after the first sensitization. Two weeks after the final sensitization, inhalation test of the antigen was carried out. That is, two sensitized guinea pigs were placed in a sealed plastic box. Aerosol of 0.5% OVA solution in physiological saline generated by ultrasonic nebulizer (OMRON NE-U11B) was blown into the plastic box for 10 minutes. When dyspnea due to anaphylactic shock and severe cyanosis were observed, inhalation of the antigen was immediately stopped. Twenty four hours after this antigen challenge, the guinea pigs were sacrificed by anesthetization by intraperitoneally administering excess pentobarbital, and the lung of each animal was lavaged with 60 ml of phosphate buffered physiological saline (not containing Ca$^{2+}$ and Mg$^{2+}$: PBS(−)). The collected lung lavage was centrifuged and the cells were resuspended in PBS(−).

The total number of cells was counted using a hemocytometer. A part of the cells was subjected to Meiglyunwald-Giemsa staining and the proportion of the eosinophils was counted. The number of the eosinophils in the lung lavage was calculated therefrom. The test compound was orally administered in the form of a suspension in 0.5% sodium carboxymethylcellulose (CMC) or in 5% gum arabi one hour before the antigen challenge.

The results are shown in Table 1.

TABLE 1

| Compound | Dose | Number of Animals | Total Number of Cells ($\times 10^7$) | Number of Eosinophils ($\times 10^5$) |
|---|---|---|---|---|
| Control | | 69 | $5.18 \pm 0.31$ | $78.0 \pm 8.0$ |
| Compound of Example 1 | 3 mg/kg | 11 | $2.63 \pm 0.18^*$ | $23.0 \pm 5.5^*$ |
| | 1 mg/kg | 7 | $2.33 \pm 0.51^*$ | $19.4 \pm 9.6^*$ |

$^*P < 0.05$

EXAMPLE 8

Eosinophil Infiltration-Suppressing Activity

The eosinophil infiltration-suppressing activity of the compound obtained in Example 2 was evaluated in the same manner as in Example 2. As shown in Table 2, maleic acid salt of the compound also suppressed the infiltration of eosinophils.

TABLE 2

| Compound | Dose | Number of Animals | Total Number of Cells ($\times 10^7$) | Number of Eosinophils ($\times 10^5$) |
|---|---|---|---|---|
| Control | | 40 | $3.91 \pm 0.35$ | $129.3 \pm 15.8$ |
| Compound of Example 2 | 3 mg/kg | 39 | $3.52 \pm 0.39$ | $77.3 \pm 13.9^*$ |

$^*P < 0.05$

By using the tricyclic triazolo derivative or a pharmaceutically acceptable salt thereof according to the present invention, it is expected that prevention and therapy of allergies and inflammation, as well as other various diseases in which eosinophils are thought to participate, may be attained. Especially, they can also be used as therapeutic agents for asthma, inverminations, tumors, eosinophilic leukemia, eosinophila syndrome, eosinophilic pneumonia, and eosinophilic gastroenteritis.

We claim:

1. A pharmaceutical composition for suppressing infiltration of eosinophils comprising as an effective ingredient a tricyclic triazolo derivative of the formula (I):

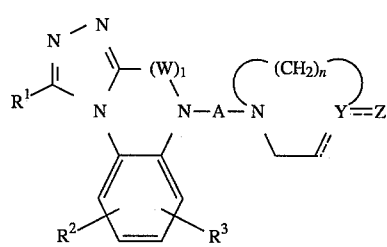

wherein $R^1$ represents hydrogen, lower alkyl, $C_3$–$C_5$ cycloalkyl or substituted or non-substituted aryl; $R^2$ and $R^3$ independently represent hydrogen, lower alkyl, lower alkoxy or halogen; W represents C=O or $CR^4R^5$ wherein $R^4$ and $R^5$ independently represent hydrogen or lower alkyl; A represents $C_1$–$C_5$ straight or branched saturated or unsaturated alkylene with the proviso that it may contain one or more hetero atoms; l represents 0 to 2, n represents 1 to 3, — represents single bond or double bond; Y represents N or C; Z represents $C(B)Ar^1Ar^2$, wherein B represents hydrogen, hydroxy or methoxy, $Ar^1$ and $Ar^2$ independently represent hydrogen or substituted or non-substituted aryl $CAr^1Ar^2$, wherein $Ar^1$ and $Ar^2$ represent the same meanings as mentioned above, O—$CHAr^1Ar^2$, wherein $Ar^1$ and $Ar^2$ represent the same meanings as mentioned above, or a condensed aromatic ring or a pharmaceutically acceptable salt thereof.

2. The pharmaceutical composition for suppressing infiltration of eosinophils according to claim 1, wherein said Z in said formula (I) is selected from the group consisting of

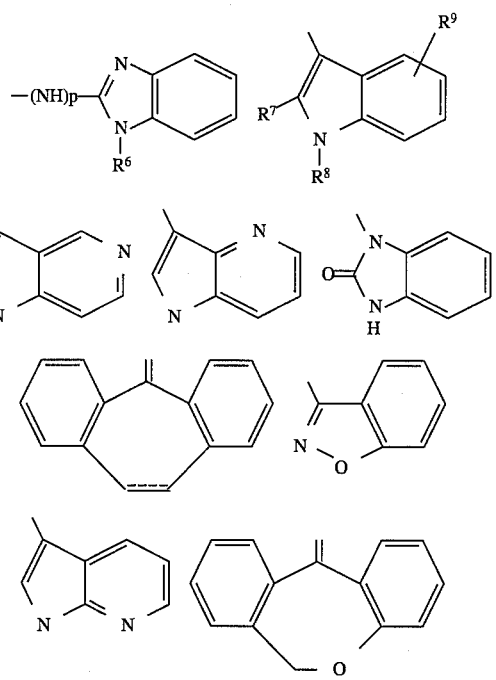

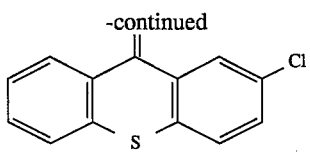

wherein $R^6$ represents substituted or non-substituted aralkyl or alkoxyalkyl; p represents 0 or 1, $R^7$ and $R^8$ independently represent hydrogen or lower alkyl; $R^9$ represents hydrogen, lower alkyl, lower alkoxy or halogen; and — represents single bond or double bond.

3. A method of suppressing infiltration of eosinophils in a patient in need thereof, comprising administering to said patient an eosinophil infiltration suppressing effective amount of the pharmaceutical composition of claim 2.

4. A method of suppressing infiltration of eosinophils in a patient in need thereof, comprising administering to said patient an eosinophil infiltration suppressing effective amount of the pharmaceutical composition of claim 1.

5. The pharmaceutical composition for suppressing infiltration of eosinophils according to claim 1, wherein said A in said formula (I) is selected from the group consisting of

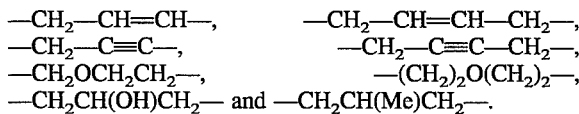

6. A method of suppressing infiltration of eosinophils in a patient in need thereof, comprising administering to said patient an eosinophil infiltration suppressing effective amount of the pharmaceutical composition of claim 5.

7. The pharmaceutical composition for suppressing infiltration of eosinophils according to claim 1, wherein said $Ar^1$ and $Ar^2$ in said formula (I) is $C_6$–$C_{10}$ aryl; or an aromatic heterocyclic group selected from the group consisting of pyridyl, pyrimidyl, thienyl and furyl, with the proviso that said aryl and aromatic heterocyclic group may be substituted with 1–3 substituent groups selected from the group consisting of $C_1$–$C_6$ alkyl, $C_1$–$C_6$ alkoxy, halogen, $C_1$–$C_6$ halogenated alkyl, $C_1$–$C_6$ alkylamino and nitro.

8. A method of suppressing infiltration of eosinophils in a patient in need thereof, comprising administering to said patient an eosinophil infiltration suppressing effective amount of the pharmaceutical composition of claim 7.

* * * * *